United States Patent [19]

Finkenaur

[11] Patent Number: 4,717,717

[45] Date of Patent: Jan. 5, 1988

[54] STABILIZED COMPOSITIONS CONTAINING EPIDERMAL GROWTH FACTOR

[75] Inventor: Amy L. Finkenaur, Somerville, N.J.

[73] Assignee: Ethicon, Inc., Somerville, N.J.

[21] Appl. No.: 927,627

[22] Filed: Nov. 5, 1986

[51] Int. Cl.[4] .................... C07K 13/00; A61K 35/22; A61K 37/36

[52] U.S. Cl. ........................ 514/21; 424/99; 424/100; 514/2; 530/399; 530/808; 530/834; 530/854

[58] Field of Search ................ 530/399, 808; 514/2, 514/21; 424/99, 100

[56] References Cited

U.S. PATENT DOCUMENTS

| | | | |
|---|---|---|---|
| 3,883,497 | 5/1975 | Gregory et al. | 424/99 X |
| 3,948,875 | 4/1976 | Cohen et al. | 424/85 X |
| 4,188,375 | 2/1980 | Straub | 424/88 |
| 4,373,519 | 2/1983 | Errode et al. | 128/156 |
| 4,528,186 | 7/1985 | Nishimura et al. | 514/2 X |
| 4,621,052 | 11/1986 | Sugimoto | 530/399 X |

FOREIGN PATENT DOCUMENTS

WO85/00369 1/1985 PCT Int'l Appl. .

OTHER PUBLICATIONS

Urdea et al., Proc. Natl. Acad. Sci. USA, 80, 7461-7465 (1983).
Lawn et al., Cell, 15, 1157-1174 (1978).
Savage et al., J. Biol. Chemistry, 247, 7612-7621 (1972).
Carpenter et al., Experimental Cell Research 164, 1-10 (1986).
Arakawa et al., Biochemistry, 21, 6536-6544 (1982).

*Primary Examiner*—Howard E. Schain

[57] ABSTRACT

Medicinal compositions containing epidermal growth factor are stabilized against loss of biological activity in the presence of moisture by including in said compositions a stabilizing amount of water-soluble cellulose polymer, preferably methylcellulose or a hydroxy alkylcellulose such as hydroxypropyl methylcellulose.

12 Claims, No Drawings

STABILIZED COMPOSITIONS CONTAINING EPIDERMAL GROWTH FACTOR

The invention relates to a means for stabilizing compositions containing epidermal growth factors.

BACKGROUND OF THE INVENTION

Epidermal growth factor is a polypeptide material that has mitogenic activity for a number of kinds of cells, including epithelial and mesenchymal cells. Epidermal growth factor exhibits epidermal growth promoting activity and gastric acid secretion inhibiting activity, and is therefore useful as a medicament. It has been found that epidermal growth factor loses biological activity in the presence of moisture. This is disadvantageous because such loss of activity makes it impractical to store aqueous preparations of epidermal growth factor for extended periods of time. This invention provides a means for reducing the loss of activity of epidermal growth factor in the presence of moisture.

BRIEF SUMMARY OF THE INVENTION

The invention provides a means for stabilizing medicinal compositions containing epidermal growth factor against loss of biological activity in the presence of moisture which comprises incorporating in said compositions a water-soluble cellulose polymer such as hydroxypropyl methylcellulose and methylcellulose.

THE PRIOR ART

Errede et al., in U.S. Pat. No. 4,373,519, disclose a wound dressing including an absorbent such as cellulose material (which may be carboxymethyl-cellulose), wherein the wound dressing may contain various medicaments such as epidermal growth factor.

Hess et al. in U.S. Pat. No. 3,923,599, disclose plant enzyme formulations which may include a cellulose derivative.

Straub, in U.S. Pat. No. 3,927,209, discloses a parainfluenza-3-virus composition that may include methylcellulose as a dispersing agent.

Dworschack et al., in U.S. Pat. No. 3,933,588, disclose enzymes immobilized on a cellulose derivative (DEAE cellulose) containing a quaternary ammonium compound as a stabilizer.

Diehl et al., in U.S. Pat. No. 4,011,169 disclose an enzyme-containing detergent composition containing an aminated starch or cellulose as a stabilizer.

Straub, in U.S. Pat. No. 4,188,375, discloses aqueous vaccine preparations that may contain methylcellulose as a dispersing agent. "Polysaccharides" are disclosed as "stabilizers", but it is not disclosed for what instability problem the stabilizers are added.

Akagi et al., in European Patent Application No. 0 150 067, disclose gamma-interferon stabilized with dextran or hydroxyethyl starch.

Jacobsen et al., in U.S. Pat. No. 4,540,506, disclose drain-cleaning formulations containing enzymes, which may contain hydroxyethyl cellulose as a thickener.

Arakawa and Timasheff, in Biochemistry 1982, Vol. 21, pages 6536-6544, disclose the use of sugars to stabilize proteins in aqueous media.

DETAILED DESCRIPTION OF THE INVENTION

The invention resides in the provision of stabilized compositions containing epidermal growth factor, preferably, human epidermal growth factor ("hEGF"). Epidermal growth factor and hEGF are known compositions that are either isolated from natural sources or are produced using recombinant DNA techniques. The following references describe epidermal growth factor, hEGH, and/or processes for isolating them from natural sources or producing them from rDNA techniques:

Camble et al., U.S. Pat. No. 3,914,824
Cohen et al., U.S. Pat. No. 3,948,875
Nishimura et al., U.S. Pat. No. 4,528,186
Bell, Published PCT patent application WO 85/00369
Urdea et al., Proc. Natl. Acad. Sci. USA 80, 7461-7465 (1983)
Hollenberg, "Epidermal Growth Factor-Urogastrone, A Polypeptide Acquiring Hormonal Status", Acad. Press, Inc., N.Y. (1979) pp. 90-132
Carpenter, "Epidermal Growth Factor" in: Handbook of Experimental Pharmacology, Vol. 57, Baserga, ed.
Lawn et al., "Cell" (1978) 15: 1157-1174
Savage et al., "J. Biol. Chem." (1972) 247: 7612-7621

As used in this application, "epidermal growth factor" is intended to include the class of polypeptides that have biological activity similar to that exhibited by natural human epidermal growth factor protein as measured in recognized bioassays such as the epidermal growth factor receptor binding assay described hereinbelow, and which have certain conserved amino acid residues and common positioning of disulfide bonds, as discussed by Carpenter et al. in "Epidermal Growth Factor, Its Receptor, and Related Proteins", Experimental Cell Research 164, (1986) 1-10. Thus, "epidermal growth factor" factor includes the hEGF produced by recombinant DNA techniques described by Bell, op. cit. supra, mouse EGF ("mEGF") isolated from the submaxillary glands of mice (see, for example, Cohen et al., op. cit. supra), rat EGF, natural human epidermal growth factor, which may be isolated from human urine as described by Nishimura et al., op. cit. supra, alpha-transforming growth factor, vaccinia growth factor, and bioactive derivatives and related polypeptides of any of the foregoing, including precursors that are transformed into active epidermal growth factor in situ by proteolytic processing. Human epidermal growth factor, including hEGF produced by recombinant DNA techniques, is preferred for use in the invention.

The stabilizers that are used in the invention are water-soluble cellulose derivatives such as methylcellulose. hydroxyethyl cellulose, carboxymethyl cellulose, hydroxypropyl methylcellulose, and hydroxypropyl cellulose. Methylcellulose and the hydroxyalkyl cellulose derivatives such as hydroxypropyl cellulose, hydroxyethyl cellulose, and hydroxypropyl methylcellulose are preferred.

The compositions that are stabilized in accordance with the invention are compositions containing epidermal growth factor, either in an aqueous medicinal composition such as a gel, solution, suspension, or dispersion, in which is dissolved an effective amount of the water-soluble cellulose derivative, or a lyophilized or other dehydrated derivative thereof which can be reconstituted by the addition of water. The exact amount of the cellulose derivative to be used in specific cases will vary, depending on factors such as presence or absence of other materials in the formulation, specific nature of the particular epidermal growth factor used, concentration of the epidermal growth factor, type of formulation, and the like. Expressed in terms of an aqueous formulation containing epidermal growth factor (either an initial formulation or a formulation that has been reconstituted following dehydration), the effective amount of the cellulose derivative will usually be at least 0.05 weight percent, based on weight of the whole composition. The maximum amount used is not at all critical, and will be in part determined by the type of formulation. For instance, an aqueous eye drop formulation will usually use an amount of the cellulose derivative within the range of from about 0.05 to about 3 weight percent. In a gel, in which a relatively small amount of water might be used, the cellulose derivative can be the major constituent of the formulation, in some cases, as much as, e.g., about 90 weight percent of the formulation. The important factor is to use at least the minimum amount of cellulose derivative that has a stabilizing effect.

The stabilized compositions of the invention are useful in eye drop formulations, salves for wound healing, gel formulations, foams, and the like. Additional materials such as buffers, preservatives, tonicity adjusting agents, anti-oxidants, other polymers (used, e.g., to adjust viscosity or as extenders), and excipients may be used in the stabilized compositions of the invention. Specific illustrative examples of such other materials include phosphate, citrate, or borate buffers, thimerosal, sorbic acid, methyl or propyl paraben, and chlorobutanol preservatives, sodium chloride and/or sugars to adjust the tonicity, polyvinyl alcohol, poly(acrylic acid) or salts thereof, polyvinyl pyrrolidone, mannitol, lactose, sucrose, ethylene diamine tetra-acetic acid, and the like.

The concentration of epidermal growth factor in the formulation is usually within the range of from about 0.001 to about 100 micrograms per milliliter of aqueous formulation (that is, either the initial aqueous formulation or a formulation that has been reconsitituted after dehydration).

In the examples reported below, the biological activity of stabilized and unstabilized aqueous epidermal growth factor formulations was assayed by the receptor binding assay method of Savage et al., Analytical Biochem., 111, pages 195 et seq. (1981). Briefly, the receptor binding assay procedure is the following:

The receptor binding assay is based on the ability of human EGF to compete with $^{125}$I-labeled mouse epidermal growth factor for binding sites on human cells. The binding is performed on confluent monolayers of formalin fixed human epidermal carcinoma A431 cells [Ref.—Fabricant et al., Proc. Natl. Acad. Sci. USA, Vol. 74, p. 565 (1977), Haigler et al., Proc. Natl. Acad. Sci. USA, Vol. 75, p. 3317 (1978), and Ullrich et al., Nature, Vol. 309, p. 418 (1984)] which possess 10–50 times more EGF receptors on their surface than most other cell types. Labelled mouse epidermal growth factor ($^{125}$I-EGF) obtained from Amersham is used.

Multidishes containing a plurality of wells are used. Each well has a confluent monolayer of the formalin fixed human epidermal carcinoma A431 cells at the bottom. First, into each well is added 80 microliters of PBS diluent (phosphate buffered saline containing 0.1 weight percent bovine serum albumin and 0.2M glycine) containing either known standard epidermal growth factor, the sample to be assayed, or a control containing no epidermal growth factor. Serial dilutions of the standard and sample reagents are usually employed. Next, 20 microliters of the $^{125}$I-EGF of a known activity and concentration in PBS is added to each well. (It is important that the reagent additions be made in the sequence given.) The wells are covered and incubated at 37° C. for about 1¼ to 2½ hours.

The reaction mixture in each well is aspirated to discard the liquid, each well is washed twice with PBS, and the wash liquid is discarded. One hundred microliters of 0.1N NaOH, 1 weight percent sodium dodecyl sulfate, is added to each well. The wells are incubated at 37° C. for 10 minutes, and then the samples are transferred individually to gamma-ray counter vials. The vial with the sample is placed in the gamma ray counter and the number of gamma rays is counted for one minute. Alternatively, multidishes containing removable wells may be employed, in which case, after the washing step, the entire well is removed and placed in the gamma ray counter for counting.

The counts from a serial dilution of a freshly prepared known EGF standard are plotted as a function of EGF concentration on a log-log graph, with the counts per minute being the Y-axis and the concentration being the X-axis. The counts per minute will be inversely proportional to the concentration of the known epidermal growth factor. The curves found for the unknown samples at known dilutions are compared against the curve for a freshly prepared known standard to determine the concentration of active EGF (in micrograms per milliliter) in each unknown sample. Values obtained from duplicates and serial dilutions are averaged to improve the accuracy.

STABILITY STUDIES

Materials and Methods

Pharmaceutical grade polymers were obtained from the following sources:

Poly(vinyl alcohol)—Gelvatol 40/20—Monsanto ("PVA")

Methylcellulose—Methocel A4M—Dow ("MC")

Hydroxypropyl methylcellulose—Methocel E4M-Dow ("HPMC")

Poly(vinyl pyrrolidone)—Plasdone C15—GAF ("PVP")

Polymer solutions were prepared to give viscosities similar to those currently used in ophthalmic formulations. The solutions also contained 0.01 weight percent thimerosal to inhibit bacterial growth and 0.9 weight percent NaCl to make them isotonic. The solutions were filtered through a 0.2 micron polysulfone filter to sterilize them. The filtered solutions were stored in sterile glass vials. epidermal growth factor produced as described in Bell, WO 85/00369, was added to each vial to give a theoretical concentration of 12 micrograms per milliliter. Two control solutions were also used; one contained epidermal growth factor in pure distilled water, and the other contained epidermal growth factor in distilled water containing only the thimerosal plus NaCl. Table I displays the concentrations and intrinsic viscosities at 25° C. of the four polymer solutions;

TABLE I

| Polymer | Concentration, wt. % | Intrinsic Viscosity, dl/gm |
|---|---|---|
| PVA | 1.4 | 0.24 |
| MC | 0.25 | 6.86 |
| HPMC | 0.25 | 6.20 |
| PVP | 1.4 | 0.16 |

The epidermal growth factor activities of the six solutions were determined by the receptor binding assay procedure described above for the freshly made solutions, and at 6, 21, and 48 days after preparation. The solutions were stored during the test in the vials at 37° C.

Table II, below, displays the activities (expressed as micrograms of active epidermal growth factor per milliliter) for the six solutions, both as made and at the 6, 21, and 48 day intervals, and the percent of the original activity remaining after 48 days.

TABLE II

RECEPTOR BINDING ACTIVITY

| Solution | Day 0 | Day 6 | Day 21 | Day 48 | % of original activity after 48 days |
|---|---|---|---|---|---|
| Water | 10.6 ± 1.0 | 10.5 ± 1.5 | 10.6 ± 1.2 | 6.6 ± 0.5 | 62 |
| Thimerosal/NaCl | 12.3 ± 0.7 | 15.3 ± 4.0 | 12.8 ± 1.2 | 6.8 ± 2.1 | 55 |
| PVA | 16.1 ± 3.5 | 14.3 ± 1.1 | 4.3 ± 2.4 | 7.6 ± 0.4 | 47 |
| MC | 18.6 ± 5 | 12.3 ± 2.3 | — | 16.8 ± 0.6 | 90 |
| HPMC | 17.4 ± 6 | — | — | 21.4 ± 4 | 100 |
| PVP | 12.3 ± 4.0 | 10.9 ± 0.1 | 6.1 ± 0.02 | 5.0 ± 1.4 | 41 |

As can be seen by the results displayed above, the aqueous epidermal growth factor solutions containing the two cellulose derivatives lost none of their biological activity (within experimental error) after storage for 48 days, whereas the others lost approximately one-half of their biological activity after the same period of time.

What is claimed is:

1. A sterile aqueous medicinal composition containing epidermal growth factor and an amount of a water-soluble cellulose polymer sufficient to stabilize said epidermal growth factor against loss of biological activity.

2. The composition of claim 1 wherein the cellulose polymer is hydroxypropyl cellulose, methylcellulose, hydroxyethyl cellulose, or hydroxypropyl methylcellulose.

3. The composition of claim 1 wherein the epidermal growth factor is human epidermal growth factor.

4. The composition of claim 2 wherein the epidermal growth factor is human epidermal growth factor.

5. A sterile composition comprising a dehydrated derivative of the composition of claim 1.

6. A sterile composition comprising a dehydrated derivative of the composition of claim 2.

7. A sterile composition comprising a dehydrated derivative of the composition of claim 3.

8. A sterile composition comprising a dehydrated derivative of the composition of claim 4.

9. A method for stabilizing an aqueous medicinal composition containing epidermal growth factor as an active ingredient, which method comprises incorporating in said composition an amount of a water-soluble cellulose polymer sufficient to stabilize said epidermal growth factor against loss of biological activity in the presence of moisture.

10. The method of claim 9 wherein said cellulose polymer is hydroxypropyl cellulose, hydroxyethyl cellulose, methylcellulose, or hydroxypropyl methylcellulose.

11. The method of claim 9 wherein said epidermal growth factor is human epidermal growth factor.

12. The method of claim 10 wherein said epidermal growth factor is human epidermal growth factor.

* * * * *